US011187633B2

(12) United States Patent
Welker (10) Patent No.: US 11,187,633 B2
(45) Date of Patent: Nov. 30, 2021

(54) LIQUEFIED NATURAL GAS VAPORIZATION SAMPLING SYSTEM

(71) Applicant: Welker, Inc., Sugar Land, TX (US)

(72) Inventor: Josh H. Welker, Richmond, TX (US)

(73) Assignee: Welker, Inc., Sugar Land, TX (US)

(*) Notice: Subject to any disclaimer, the term of this patent is extended or adjusted under 35 U.S.C. 154(b) by 222 days.

(21) Appl. No.: 16/574,347

(22) Filed: Sep. 18, 2019

(65) Prior Publication Data

US 2021/0080363 A1 Mar. 18, 2021

(51) Int. Cl.
*G01N 1/44* (2006.01)
*G01N 33/28* (2006.01)

(52) U.S. Cl.
CPC ............... *G01N 1/44* (2013.01); *G01N 33/28* (2013.01)

(58) Field of Classification Search
CPC .............. G01N 1/10; G01N 2001/105; G01N 33/0016; G01N 1/22; G01N 1/44; G01N 33/225; G01N 1/2247
See application file for complete search history.

(56) References Cited

U.S. PATENT DOCUMENTS

| | | | | |
|---|---|---|---|---|
| 3,824,858 A | * | 7/1974 | Erdman | G01N 1/10 73/864.91 |
| 5,637,809 A | * | 6/1997 | Traina | G01N 1/2258 73/864.12 |
| 7,162,933 B2 | * | 1/2007 | Thompson | G01N 1/2214 73/863.11 |
| 7,337,616 B2 | * | 3/2008 | Meneses | F17C 13/02 422/50 |
| 7,484,404 B2 | | 2/2009 | Thompson et al. | |
| 7,882,729 B2 | * | 2/2011 | Thompson | G01N 33/225 73/61.57 |
| 8,056,399 B2 | * | 11/2011 | Thompson | G01N 1/10 73/61.59 |
| 8,347,694 B2 | | 1/2013 | Welker et al. | |
| 8,713,995 B2 | * | 5/2014 | Thompson | F17C 9/00 73/61.57 |
| 8,800,394 B2 | * | 8/2014 | Bombulie | G01N 1/2042 73/864.62 |
| 9,057,668 B2 | * | 6/2015 | Thompson | G01N 1/22 |
| 9,164,016 B2 | * | 10/2015 | Barere | F17C 9/02 |
| 9,285,299 B2 | * | 3/2016 | Thompson | G01N 1/2247 |
| 9,562,833 B2 | * | 2/2017 | Thompson | G01N 1/2247 |
| 9,625,431 B2 | * | 4/2017 | Thompson | G01N 1/10 |
| 10,078,035 B2 | * | 9/2018 | Curtis | G01N 1/14 |
| 10,088,394 B2 | * | 10/2018 | Thompson | F16K 27/12 |

(Continued)

*Primary Examiner* — David A. Rogers
(74) *Attorney, Agent, or Firm* — Husch Blackwell LLP (57) ABSTRACT

An improved liquefied natural gas vaporization system is provided for converting liquefied natural gas (LNG) to vapor so that it can be measured for integrity. The liquefied natural gas vaporization system of the present invention makes use of a sample probe that uses a cryogenic check valve to allow the vaporization process to begin early, and, due to design and incorporation with heated regulation, reduces the need for an accumulator, which is often used in other systems. By eliminating the need for an accumulator, a more real-time and authentic measurement of the LNG sample may be taken. After the probe takes the sample, the sample is sent to a sampling system and subsequently to an analytical measuring system, where the sample is measured.

9 Claims, 4 Drawing Sheets

(56) References Cited

U.S. PATENT DOCUMENTS

| | | | |
|---|---|---|---|
| 10,281,368 B2* | 5/2019 | Thompson | G01N 1/10 |
| RE47,478 E* | 7/2019 | Thompson | G01N 1/2247 |
| 10,429,278 B2* | 10/2019 | Thompson | G01N 1/18 |
| 10,613,006 B1* | 4/2020 | Thompson | G01N 33/28 |
| 10,921,225 B2* | 2/2021 | Thompson | G01N 33/28 |
| 2003/0228707 A1* | 12/2003 | Meneses | F25J 3/04412 62/48.1 |
| 2006/0201235 A1* | 9/2006 | Thompson | G01N 1/22 73/61.59 |
| 2009/0145206 A1* | 6/2009 | Thompson | F17C 13/02 73/61.59 |
| 2009/0151427 A1* | 6/2009 | Thompson | F17C 6/00 73/23.41 |
| 2010/0012201 A1* | 1/2010 | Welker | F16K 15/028 137/535 |
| 2011/0192237 A1* | 8/2011 | Bombulie | G01N 1/42 73/863.11 |
| 2012/0017669 A1* | 1/2012 | Thompson | F17C 9/00 73/61.59 |
| 2013/0074581 A1* | 3/2013 | Blacklin | G01N 1/14 73/23.41 |
| 2013/0263680 A1* | 10/2013 | Barere | G01N 1/10 73/863.12 |
| 2013/0312542 A1* | 11/2013 | Rolston | G01D 11/24 73/863.12 |
| 2014/0144254 A1* | 5/2014 | Thompson | G01N 1/2247 73/863.11 |
| 2014/0230521 A1* | 8/2014 | Thompson | F17C 13/02 73/19.1 |
| 2014/0260695 A1* | 9/2014 | Thompson | F16K 27/12 73/863.81 |
| 2014/0311213 A1* | 10/2014 | Thompson | G01N 1/18 73/23.2 |
| 2017/0082524 A1* | 3/2017 | Curtis | G01N 1/14 |
| 2017/0167954 A1* | 6/2017 | Thompson | G01N 1/20 |
| 2019/0041298 A1* | 2/2019 | Rolston | G01N 1/2202 |
| 2020/0096426 A1* | 3/2020 | Thompson | G01N 1/44 |
| 2020/0158608 A1* | 5/2020 | Thompson | H05B 3/06 |
| 2020/0326320 A1* | 10/2020 | Querrey | G01N 1/2247 |
| 2021/0140859 A1* | 5/2021 | Thompson | G01N 1/44 |

* cited by examiner

FIG. 2

PRIOR ART

FIG. 4

LIQUEFIED NATURAL GAS VAPORIZATION SAMPLING SYSTEM

FIELD OF THE INVENTION

This invention generally relates to a system for vaporizing a liquefied natural gas (LNG) sample and subsequently measuring it for its quality. More particularly, the current invention relates to a system for using a probe to sample and allow the vaporization of LNG into a gas form (vaporized liquefied natural gas) to begin in order to determine its constituent components and measure the British Thermal Unit (BTU) value of an LNG shipment and streamline the process.

BACKGROUND OF THE INVENTION

Natural gas is a naturally occurring hydrocarbon gas mixture consisting primarily of methane. However, it may also include varying amounts of other higher alkanes and typically a small percentage of ethane, propane, butane, and nitrogen. Natural gas may be formed by methanogenic organisms in marshes, bogs, landfills, and shallow sediments, or from buried organic material. For example, layers of decomposing plant and animal matter exposed to intense heat and pressure under the surface of the Earth over extended periods of time may become natural gas.

Natural gas is commonly used as a source of energy for heating, cooking, and generating electricity. It is also used as a fuel for vehicles and other manufacturing processes.

Natural gas is most often measured in British thermal units, or BTU. One BTU is the amount of heat needed to raise the temperature of a pound of water by one degree Fahrenheit at atmospheric pressure.

Natural gas is typically extracted from the earth using drilling processes before eventually being sold to purchasers. Production companies explore, drill, and extract natural gas from the ground. After that, transmission companies transmit the natural gas via pipelines to areas where consumers are located. Finally, distribution companies transport natural gas to the customer.

There are nearly 200 million consumers of natural gas in the United States alone. Natural gas is delivered to those consumers through a network of underground pipes that extends over a million miles. To produce and deliver this natural gas, over 250,000 natural gas wells and more than a thousand local distribution companies providing that gas service are spread across the country.

Natural gas is a significant driver in the U.S. economy and a very prominent natural energy source for American consumers. In recent history, for a variety of reasons, industry has looked to alternative ways to transport natural gas. One solution that has gained momentum is the use of liquefied natural gas (LNG). LNG has since become a viable solution for the United States to export internationally or import. LNG is an attractive import/export option because it can be efficiently shipped in greater quantities than natural gas in its gaseous state.

Natural gas is converted to LNG by removing impurities from the natural gas before liquefying it. Natural gas is liquefied by reducing it to very low temperatures, approximately negative 260° F. By liquefying natural gas, it takes up a fraction (approximately a 1:600 ratio) of the volume as natural gas in its gaseous form. As such, vast quantities of LNG can be imported on large double-hulled ships. Upon delivery onshore, the LNG may be off-loaded into storage tanks before being vaporized at high temperatures to reconvert it to its gaseous state. In its gas form, converted LNG may be delivered to end users via established natural gas pipelines already in use for domestically produced natural gas.

LNG is typically measured for its worth by its BTU, often using chromatography techniques. Thus, shipments of LNG are often analyzed to ensure that the BTU tied to the sale price is accurate upon delivery. BTU values often fluctuate during shipment, and purchasers want to ensure that the LNG it receives is "as advertised." Information regarding energy loss is also relevant to ship operators because they may be economically responsible for such energy losses. Thus, ship operators may look to certain energy saving techniques if energy loss is too great.

One possible solution is provided in U.S. Pat. No. 7,484,404 titled LIQUID GAS VAPORIZATION SYSTEM AND METHOD. However, that solution involves the use of an accumulator. Common to many systems, the accumulator stores excess expanded gas that is created when the vaporizer takes in a sample of LNG to vaporize and measure. The accumulator makes the system cumbersome and less efficient because it requires extra space and cost to operate the accumulator while the vaporizer system is in use.

The extra time is known in the industry as lag time. For example, lag time is created in the prior art system because time is taken to hold the LNG in gas form in the accumulator. This lag time causes the system to ultimately capture a sample that may not be representative, as the sample loses some integrity over time in the accumulator. This is undesirable because capturing the sample in as close to real time as possible makes for the most representative sample.

Accordingly, it is desired to provide a system for measuring the BTU value of an LNG shipment as it is off-loaded from a tanker ship. The system should be efficient and accurate.

SUMMARY OF THE INVENTION

The present invention is a novel liquefied natural gas sampling system for efficiently and accurately sampling and measuring liquefied natural gas for its energy content. The system utilizes a sampling probe that allows for the vaporizing process to begin downstream of the probe inlet check. Because the sample is taken in near real time, the sample measured by the sampling system is more representative of the LNG supply and is thus more accurate.

LNG may be sampled to determine its energy level, most often using BTU as a unit of measurement. To initiate that process, a sample probe captures a sample from the supply. Within the sample probe, and substantially instantaneously, the sample is allowed to vaporize to a certain degree before eventually being sent to the vaporizing portion of the sampling system and on to an analyzer system, like a chromatograph, to measure its value. Early vaporization reduces lag time of the sample so that more representative samples may be taken for measurement.

At one end of the sample probe, which is embodied by U.S. Pat. No. 8,347,694, a unique inlet is provided into which the sample is introduced. The sample probe is preferably made of stainless steel, but in alternative embodiments may be made from a number of alternative materials that are preferably thermally conductive and efficient. The probe is principally cylindrical with the exception of certain valves and connection points described below.

Near the inlet, the probe preferably includes a cryogenic check valve assembly that closes when LNG begins to vaporize within the sample probe, tubing run, and cabinet.

With the check valve closed, heavier components within the LNG sample may be prevented from being pushed back into the pipeline. This will preserve the integrity of the LNG sample. The check valve may be accessed when necessary for cleaning and/or maintenance purposes.

The sample probe preferably includes a central shaft having a bore tunneling therethrough. The sample may flow through the bore after entering the sample probe. Toward a central portion of the sample probe's shaft, an isolation flange may be provided that may be installed to the pipeline to secure the probe to the pipeline. At least one pressure relief device may also be present on the probe to allow for excess pressure built up within the sample probe to be relieved during use or to depressurize the probe when removed for cleaning or maintenance.

An outlet is preferably provided distal to the probe's inlet. The outlet may be controlled by a valve to open and close the outlet. When the valve is open, the sample within the probe may be provided to a sampling system to further process the sample prior to measuring the integrity of the sample. Flow may then continue within the probe until the outlet valve is closed.

When a sample is provided, the sample probe allows by design the liquefied natural gas to begin to change phase and become a gas. As such, no accumulator, a common and often problematic component of prior art sampling systems, is included in the sampling system. This improves the integrity of the sample as a result.

Near the inlet, a ball check valve including a spring and ball is provided that operates to close the valve when a different predetermined pressure increase is reached in the probe and to open the valve when a certain decreased pressure is reached in the probe. The valve closing helps to prevent a sample that has already been introduced to the probe from being sent back to the supply. This spring and ball check valve system preferably allows for continuous input of an LNG sample when the valve member is open on the sample probe so that the LNG sample is captured in or at near real time.

The sampling system that receives the sample after it has passed through the probe preferably includes an inlet port that is in fluid communication with the outlet of the sample probe.

Within the sampling system, a number of heaters may be provided to further heat and vaporize the already somewhat vaporized LNG sample. Similarly, valves may be provided to relieve excess pressure within the sampling system. After having been heat- and pressure-regulated, the sample may flow to an analytical measuring device, such as a chromatograph, for analysis of the sample.

BRIEF DESCRIPTION OF THE DRAWINGS

For a better understanding of the present invention, reference may be made to the following accompanying drawings.

DETAILED DESCRIPTION OF THE INVENTION

Figure 1:
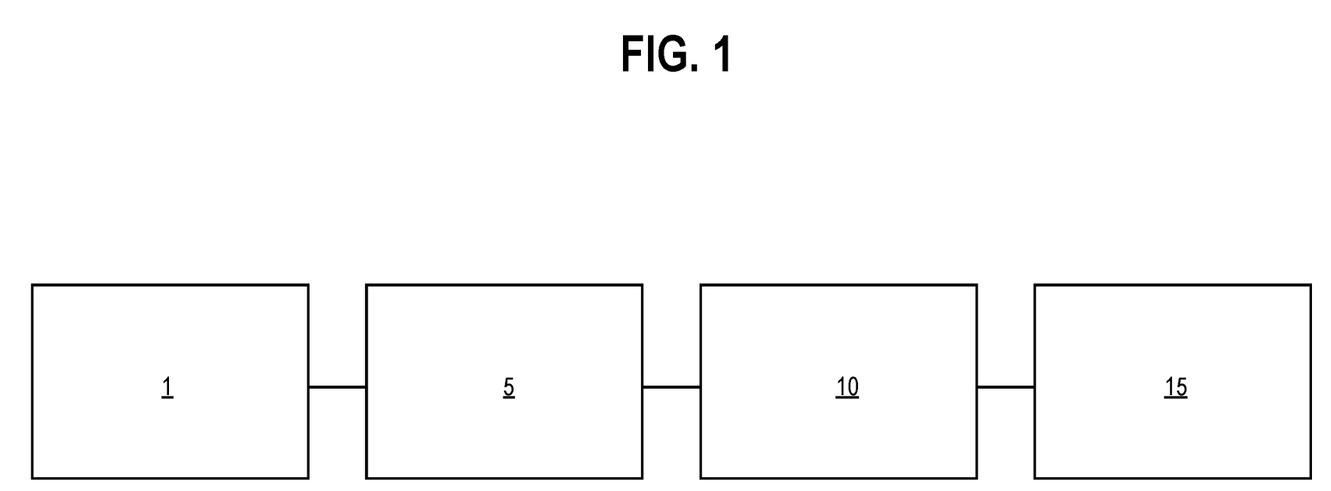
FIG. 1 is a process drawing of a liquefied natural gas vaporization sampling system, including a liquefied natural gas supply, a sample probe, a sampling system, and an analytical measuring device.

Turning first to FIG. 1, a drawing is provided that illustrates the process by which the subject liquefied natural gas vaporization system operates. In FIG. 1, a liquefied natural gas (LNG) supply 1 is provided that may be of the type that a purchaser, ship operator, or other LNG supplier, transporter, distributor, or recipient may wish to sample to determine its energy level, most commonly using British thermal units (BTU) as a unit of measurement. A sample probe 5 is used to capture a sample from the supply 1 and allow the vaporization of the sample to begin while the sample is being sent to the sampling system 10. The sampling system 10 processes the sample in the manner described below in greater detail and eventually sends it to an analytical measuring device 15, for example a chromatograph machine, so that the sample may be measured, for example by measuring its BTU.

Figure 2:
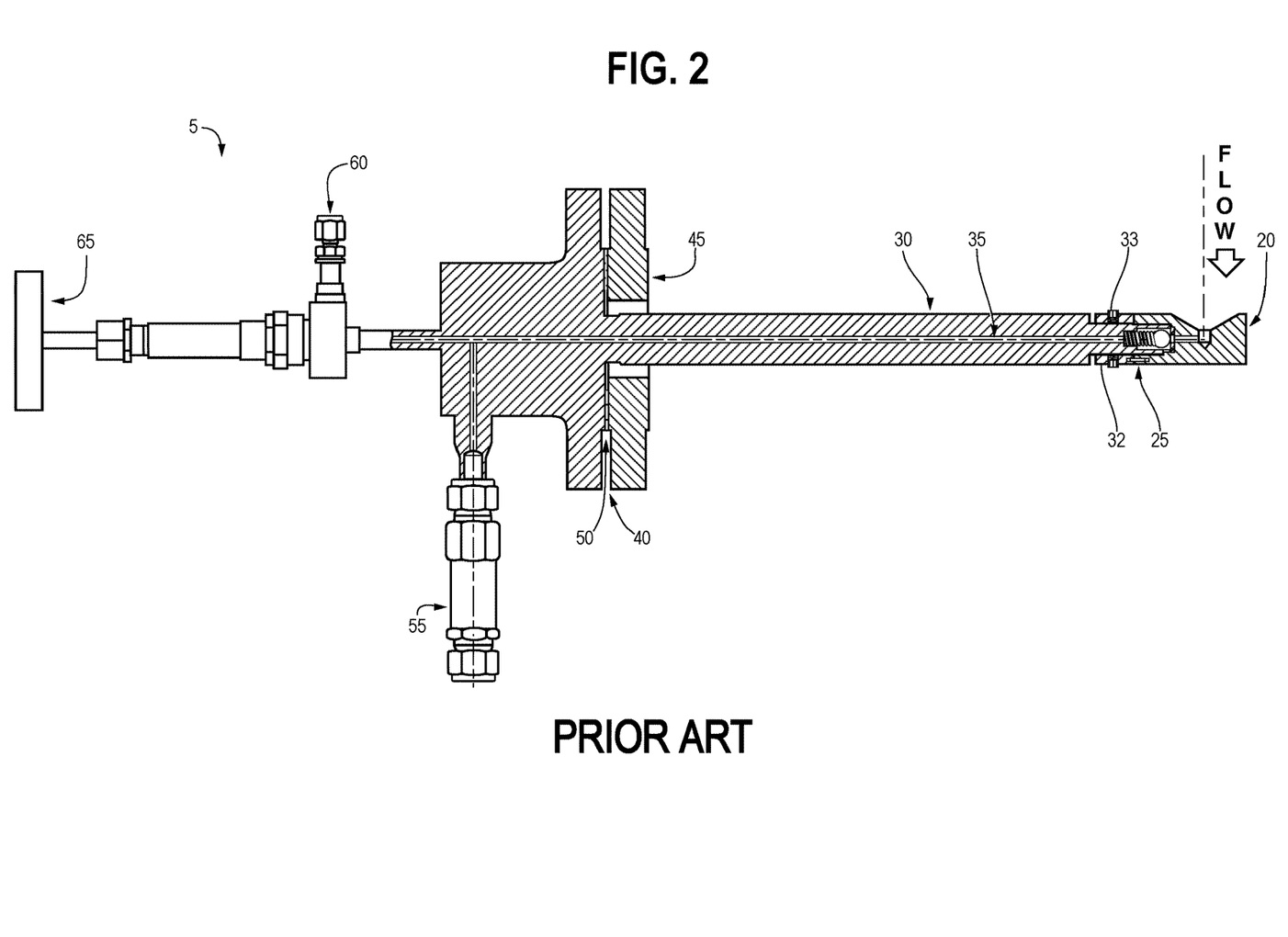
FIG. 2 is a schematic of the sample probe of the LNG sampling system of FIG. 1.

The sample probe 5 is shown in greater detail in FIG. 2. At one end of the sample probe 5, an inlet 20 is preferably provided through which an LNG sample may flow prior to being processed by the sampling system 10 by the process described below. In a preferred embodiment, the probe 5 is provided with a tip assembly (not illustrated) that is in fluid communication with the inlet 20 and may be inserted into a pipeline so as to place the inlet 20 in fluid communication with the LNG flow of the pipeline so that a sample may be obtained from a supply source at the inlet 20.

In the preferred embodiment, the probe 5 may be made of stainless steel. However, in alternative embodiments contemplated herein, other materials may be used. In any embodiment, it is preferred that the material used for the probe 5 be thermally conductive to increase the probe's thermal efficiency. The probe 5 preferably primarily consists of a generally cylindrical body, although as will be discussed hereinbelow, various portions of the sample probe 5 may vary in diameter and have threaded outward projections for the purpose of coupling the probe 5 to the sampling system 10 or the pipeline. Near the inlet 20, the probe 5 preferably includes a check valve assembly 25. The check valve assembly 25 preferably closes when LNG begins to vaporize and expand within the sample probe 5 and the sampling system 10. The check valve 25 closing will prevent heavier components within the LNG sample from being pushed back into the pipeline, thus preserving the representativeness of the LNG sample going to the analyzer. The check valve assembly 25 is illustrated in greater detail in FIG. 3 and also discussed in greater detail below.

Downstream from the check valve assembly 25, the sample probe 5 is preferably provided with a shaft 30 through which the sample may flow after having entered the sample probe 5 by way of the inlet 20. The shaft 30 preferably includes an axial bore 35 throughout its length that is in fluid communication with the inlet 20. Between the inlet 20 and the axial bore 35 through which that sample may subsequently flow, a lock collar 32 and plurality of setscrews 33 (one of which is illustrated in FIG. 2) may be provided to allow a user to access the check valve 25 and its associated seat and ball described below. Access to the check valve 25 may be required for maintenance or cleaning purposes.

Toward a central portion 40 of the sample probe 5, an isolation flange 45 is preferably provided that may be installed to the pipeline. A gasket 50 substantially similar to those known in the art may further be used to secure the sample probe 5 to the pipeline by way of the isolation flange 45.

Downstream from the isolation flange 45, the sample probe 5 is preferably provided with a pressure relief device 55. The pressure relief device 55 is preferably in fluid communication to a flare or drain. When excess pressure is built up within the sample probe 5, pressure may be relieved by way of the pressure relief outlet 55. Moreover, the pressure relief device 55 may be used to depressurize the probe 5 and the pipeline (not illustrated) before removing the unit for cleaning and/or maintenance. At a distance away from the inlet 20, the probe 5 is provided with an outlet 60. The outlet 60 preferably includes fittings that are compatible with the sampling system 10. The outlet 60 is preferably associated with an outlet valve 65. The outlet valve 65 is preferably operable to open and close the outlet 60. When the outlet 60 is open, it is preferably in fluid communication with the sampling system so that a sample obtained from the sample probe 5 may be sent to the sampling system 10.

In use, to introduce a sample to the sample probe 5 and subsequently output it to the sampling system 10, the outlet valve 65 should first be slowly opened. It should be noted that the outlet valve 65 should not be opened until the sampling system 10 has been preloaded with inert gas, such as helium or argon. Otherwise, opening the valve 65 prior to the system 10 being preloaded may cause product to flood into the system 10 and thus damage it. With the outlet 60 opened by the outlet valve 65, product may flow into the sample probe via the inlet 20 and the bore 35 within the shaft 30 before being outputted at the outlet 60 into the sampling system 10. Flow may then continue continuously within the probe 5 for vaporized LNG to be sampled until the outlet valve 65 is closed.

Figure 3:
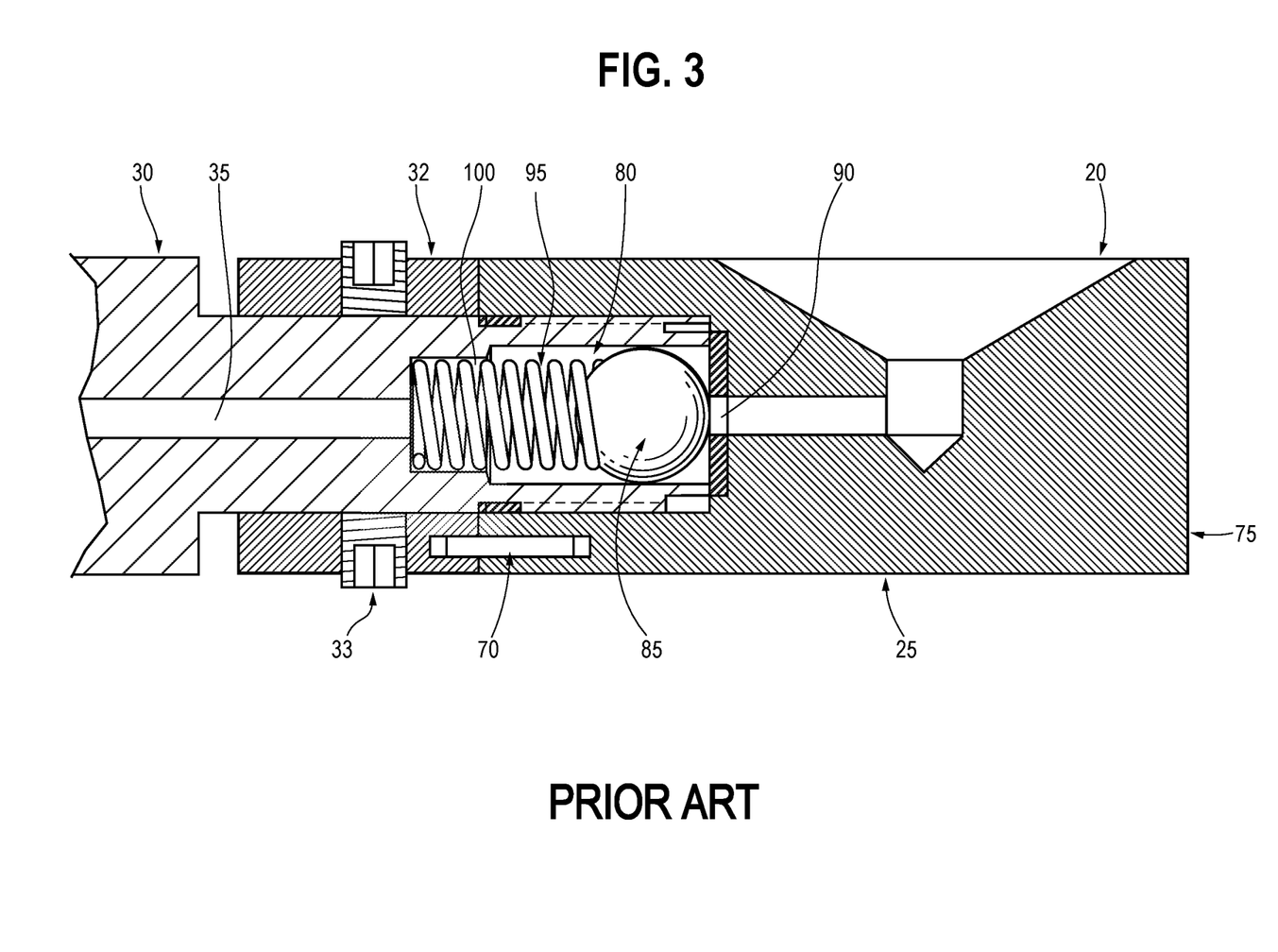
FIG. 3 is an enlarged view of a check valve assembly of the sample probe of FIG. 2.

Turning to FIG. 3, the cryogenic check valve assembly 25 of the sample probe 5 allows by design for the liquefied natural gas to begin converting to gas phase immediately when captured. This check valve 25 preferably eliminates the need for specialized insulation and tubing, common components of prior art sampling systems. In the check valve 25 shown in FIG. 3, a pin member 70 may be used to align the lock collar 32 and an inlet block member 75 in which the inlet 20 is housed. Within the shaft 30, a cavity member 80 is preferably provided having a circumference greater than that of the bore 35. Within the cavity 80, a ball member 85 is in fluid communication with the inlet 20 when the valve is closed. That way, when the ball member 85 is abutting the opening 90, no flow occurs from the inlet 20 to the outlet 60. The ball member 85 is preferably retained against the opening 90 by a spring member 95. The spring member 95 is also preferably housed within the cavity member 80. The spring member 95 is contained within the cavity member 80 such that it is housed within a recess 100 in the cavity member towards the bore 35 and abuts the ball member 85 towards the inlet 20.

In operation, when pressure is low within the bore 35, pressure from the pipeline with which the inlet 20 is associated may be greater. As such, the pressure is preferably sufficient to displace the ball member 85 away from the opening 90, thus allowing sample provided by the pipeline at the inlet 20 to be introduced into the bore 35. When pressure has amounted within the bore 35 to a sufficient degree, the ball member 85 is retained by that pressure via the spring 95 to its closed position where the ball member 85 abuts the opening 90. In this position, gas that has already been introduced to the bore 35 is preferably not returned to the inlet 20. This spring and ball check valve system preferably allows for continuous input of an LNG sample when the valve member 65 is open on the sample probe 5. This continuous sampling preferably ensures that the LNG sample is captured in or at near real time. Such a real time sample is preferred because it is more representative of the product supplied within the pipeline.

Figure 4:
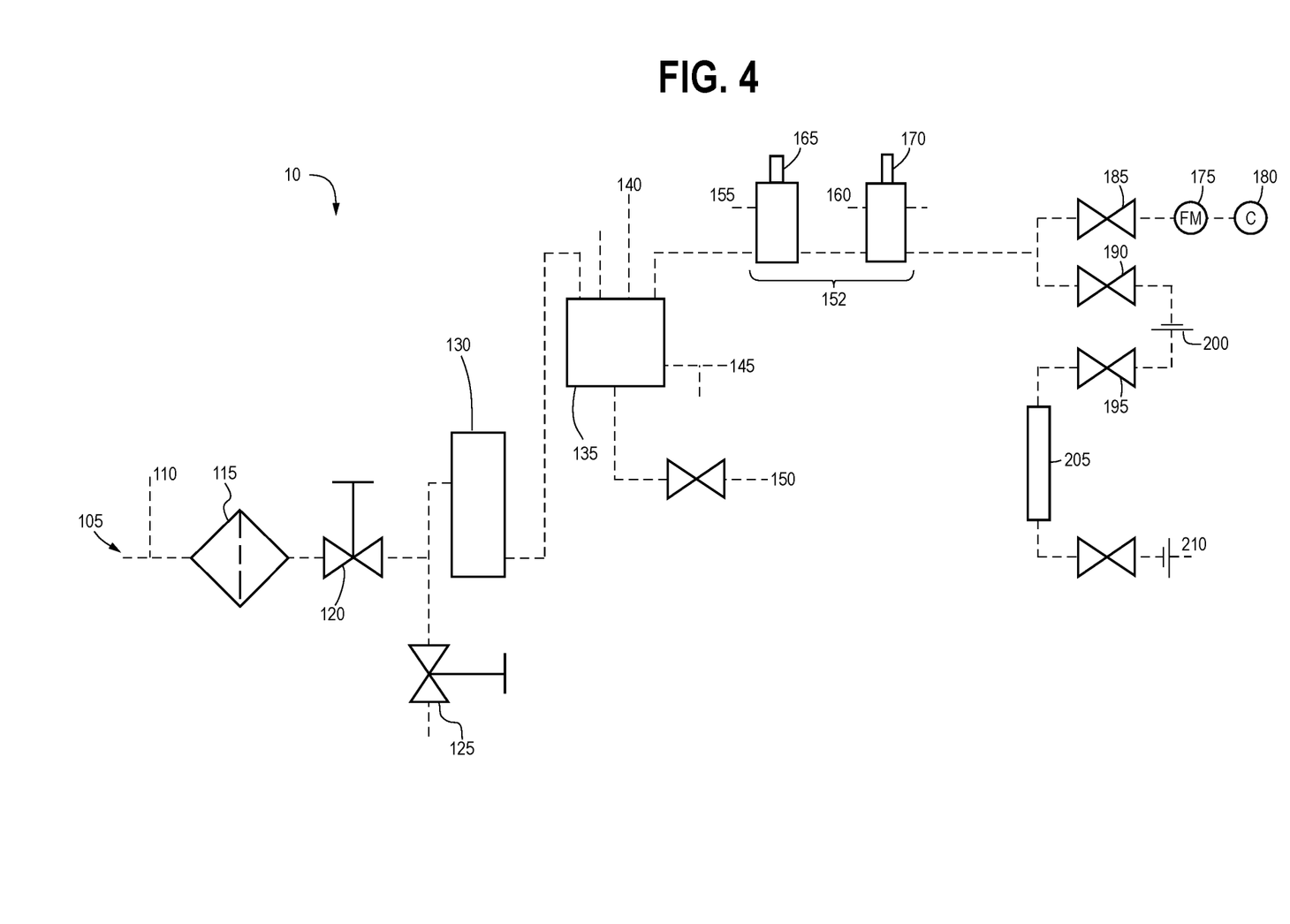
FIG. 4 is a schematic of the sampling system of FIG. 1.

Turning now to FIG. 4, the sampling system 10 of the current invention is illustrated in greater detail. The sampling system 10 preferably includes an inlet port 105 that is in fluid communication with the outlet 60 of the sample probe 5. It is at the inlet port 105 that a sample from the sample probe 5 may be received by the sampling system 10. As such, it preferably includes threads or other mechanisms that are complementary with the outlet 60 of the probe 5.

Also, a secondary check valve is adjacent the inlet port 105 prior to product entering the system 10. This provides for a second level of assurance that the sample will not return to the source during expansion and vaporization. The flare or relief valve 110 may be used to depressurize the sampling system 10 when necessary. Optionally, the sampling system 10 may be provided with a filter member 115 that filters the sample received by the system 10. Downstream therefrom, two cryogenic valves 120, 125 are provided. While in the embodiment illustrated in FIG. 4, two cryogenic valves 120, 125 are provided, in alternative embodiments, more or fewer cryogenic valves such as the valves 120, 125 may be provided. As long understood in the art, the cryogenic valves 120, 125 may be used to keep the very low temperature LNG securely and safely contained.

After being introduced to the sampling system, the already somewhat vaporized LNG may then flow through a circulation heater 130 that may be downstream from the valves 120, 125. The circulation heater 130 preferably heats up the sampled LNG so that it becomes more gaseous. The temperature of the circulation heater may range from 60 to 250 degrees Fahrenheit.

Next, the sample may be sent to a manifold 135 downstream from the circulation heater 130. At the manifold 135, the sample is measured by a resistance temperature detector (RTD) 140. The RTD sensor 140 may be readable so that an operator is able to make sure that the circulation heater 130 is working adequately. A pressure relief valve like those known and understood in the art 145 may also be in fluid communication with the manifold. Thus, if a pressure that is too high above the design pressure is sensed within the manifold 135, some of that pressure may be relieved by way of the pressure relief valve 145. Similarly, a drain member 150 is associated with the manifold 135 that may release any excess gas determined to be within the manifold 135 to a separate container or tank or sent to flare or a gaseous pipeline.

Further downstream from the manifold 135, a temperature and pressure section 152 is provided for conditioning the sample to a desired temperature and pressure. The temperature and pressure section 152 may include each of a heated regulator 155 and a pressure regulator 160. Both of the regulators 155, 160 are preferably provided with a pressure relief valve 165, 170. The pressure relief valve 165 is associated with the heated regulator 155, and the pressure relief valve 170 is associated with the pressure regulator 160. Like relief valves known in the art, the pressure relief valves 165, 170 help relieve the sampling system 10 of excess heat and/or pressure.

The heated regulator 155 preferably heats the sample for a second time, preferably to a temperature between 130 and 300 degrees Fahrenheit. Because of the excess pressure created in the sample during the vaporization process, the pressure regulator 160 preferably acts to reduce pressure to a final output pressure that is suitable for the analytical measuring device 15. After having been regulated by the heated regulator 155 and the pressure regulator 160, the sample may flow through a flowmeter 175 to an analytical measuring device, in this case a chromatograph 180, for analysis of the sample. A valve may be present between the flowmeter 175 and the pressure regulator 160. In the illustrated embodiment, that valve is valve 185. It is also understood that the heated regulator 155 and the pressure regulator 160 could be presented in the same embodiment as a single instrument.

A second valve may also be in fluid communication with the pressure regulator 160, valve 190. The valve 190 may be activated and connected with a second valve 195 by way of a quick connect structure 200. When a spot sample is generated, it is sent to a sample cylinder 205 by way of the valves 190, 195. Excess volume/purge volume is sent to drain by way of quick connect structure 210, where it may be disposed of.

It should also be noted that after use and sometimes during use, the above described probe 5 and sampling system 10 may be purged by an inert gas. This process, which may use some of the various relief valves and outlets described above, preferably dries out the probe 5 and system 10 to prevent freezing.

From the foregoing, it will be seen that the various embodiments of the present invention are well adapted to attain all the objectives and advantages hereinabove set forth together with still other advantages which are obvious and which are inherent to the present structures. It will be understood that certain features and sub-combinations of the present embodiments are of utility and may be employed without reference to other features and sub-combinations. Since many possible embodiments of the present invention may be made without departing from the spirit and scope of the present invention, it is also to be understood that all disclosures herein set forth or illustrated in the accompanying drawings are to be interpreted as illustrative only and not limiting. The various constructions described above and illustrated in the drawings are presented by way of example only and are not intended to limit the concepts, principles, and scope of the present invention.

Many changes, modifications, variations, and other uses and applications of the present invention will, however, become apparent to those skilled in the art after considering the specification and the accompanying drawings. All such changes, modifications, variations, and other uses and applications which do not depart from the spirit and scope of the invention are deemed to be covered by the invention, which is limited only by the claims which follow.

The invention claimed is:

1. A system for vaporizing and measuring liquefied natural gas, the system comprising:
a sample probe for receiving a liquefied natural gas sample from a supply, the sample probe including a cryogenic check valve that allows by design for the liquefied natural gas sample to begin vaporizing immediately upon entering the sample probe;
a sampling system for vaporizing the liquefied natural gas sample into a vapor gas, the sampling system including:
an input for receiving the liquefied natural gas sample from the sample probe;
a temperature and pressure section for conditioning the gas sample; and
an output for connection with an analytical measuring device for measuring the constituent components of the vapor gas;
wherein the sampling system includes a circulation heater that heats the liquefied natural gas sample to between 60 and 250 degrees Fahrenheit and
wherein the sampling system includes a manifold to which the liquefied natural gas sample is sent after being heated by the circulation heater.

2. The system of claim 1, wherein the sample probe and an inlet check valve assembly are in direct communication with one another.

3. The system of claim 1, wherein the sample probe includes an isolation flange that is attachable to a pipeline to secure the sample probe to the pipeline.

4. The system of claim 1, wherein a quick connect-activated valve is provided near the output of the sampling system to discharge excess vapor gas not to be measured by the analytical measuring device.

5. The system of claim 1, wherein at least one of the sample probe and the sampling system may be purged by an inert gas.

6. A system for vaporizing and measuring liquefied natural gas, the system comprising:
a sample probe for receiving a liquefied natural gas sample from a supply, the sample probe including a cryogenic check valve that allows by design for the liquefied natural gas sample to begin vaporizing immediately upon entering the sample probe;
a sampling system for vaporizing the liquefied natural gas sample into a vapor gas, the sampling system including:
an input for receiving the liquefied natural gas sample from the sample probe;
a temperature and pressure section for conditioning the gas sample; and
an output for connection with an analytical measuring device for measuring the constituent components of the vapor gas;
wherein the sampling system includes a circulation heater that heats the liquefied natural gas sample to between 60 and 250 degrees Fahrenheit and
wherein an RTD sensor associated with a manifold measures the liquefied natural gas sample in the manifold to measure the function of the circulation heater.

7. A system for vaporizing and measuring liquefied natural gas, the system comprising:
a sample probe for receiving a liquefied natural gas sample from a supply, the sample probe including a cryogenic check valve that allows by design for the liquefied natural gas sample to begin vaporizing immediately upon entering the sample probe;
a sampling system for vaporizing the liquefied natural gas sample into a vapor gas, the sampling system including:
an input for receiving the liquefied natural gas sample from the sample probe;
a temperature and pressure section for conditioning the gas sample; and
an output for connection with an analytical measuring device for measuring the constituent components of the vapor gas;
wherein the sampling system includes a circulation heater that heats the liquefied natural gas sample to between 60 and 250 degrees Fahrenheit and
wherein the temperature and pressure section includes a heated regulator that heats the liquefied natural gas sample to a temperature between 130 and 300 degrees Fahrenheit after the sample has been heated by the circulation heater.

8. The system of claim 7, wherein the temperature and pressure section includes a pressure regulator to reduce pressure of the vapor gas to a final output pressure that is suitable for the analytical measuring device.

9. The system of claim 7, wherein the sample probe, an inlet check valve, and the heated regulator eliminate the need for an accumulator.

* * * * *